United States Patent [19]
Matthews

[11] Patent Number: 5,865,850
[45] Date of Patent: *Feb. 2, 1999

[54] COATED LOAD BEARING SURFACE FOR A PROSTHETIC JOINT

[75] Inventor: Frank D. Matthews, Walpole, Mass.

[73] Assignee: Johnson & Johnson Professional, Inc., Raynham, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 814,265

[22] Filed: Mar. 10, 1997

[51] Int. Cl.⁶ .................................................. A61F 2/32
[52] U.S. Cl. .............................................. 623/23; 623/18
[58] Field of Search .................................. 623/16, 18, 19, 623/22, 23

[56] References Cited

U.S. PATENT DOCUMENTS

| | | | |
|---|---|---|---|
| Re. 32,449 | 6/1987 | Claussen et al. | 623/23 |
| 4,012,795 | 3/1977 | Doore et al. | 623/23 |
| 4,225,981 | 10/1980 | Zeibig | 623/23 |
| 4,227,265 | 10/1980 | Frey | 623/23 |
| 4,659,331 | 4/1987 | Matthews et al. | 623/20 |
| 4,778,473 | 10/1988 | Matthews et al. | 623/20 |
| 4,851,008 | 7/1989 | Johnson | 623/16 |
| 4,964,869 | 10/1990 | Auclair et al. | 623/23 |
| 5,002,581 | 3/1991 | Paxson et al. | 623/23 |
| 5,015,257 | 5/1991 | Crowninshield et al. | 623/23 |
| 5,152,794 | 10/1992 | Davidson | 623/16 |
| 5,152,795 | 10/1992 | Sioshansi et al. | 623/23 |
| 5,181,929 | 1/1993 | Prats et al. | 623/23 |
| 5,358,547 | 10/1994 | Holko | 75/254 |
| 5,362,311 | 11/1994 | Amino et al. | 623/22 |
| 5,370,694 | 12/1994 | Davisdon | 623/16 |
| 5,383,934 | 1/1995 | Armini et al. | 623/16 |
| 5,437,551 | 8/1995 | Chalifoux | 433/173 |
| 5,549,703 | 8/1996 | Daigle et al. | 623/23 |
| 5,591,313 | 1/1997 | Barber, Jr. et al. | 204/192.12 |

*Primary Examiner*—David J. Isabella
*Attorney, Agent, or Firm*—Nutter, McClennen & Fish, LLP

[57] ABSTRACT

A prosthetic hip joint includes a ceramic hip head having a bore which defines a surface, wherein the bore surface has a layer of malleable material disposed on at least a portion thereof. The surface of the bore includes surface imperfections in the form of peaks and valleys. The prosthetic hip joint can also include a femoral component having a trunnion with a tapered surface adapted for friction fit insertion into the bore of the hip head. The layer of material, such as pure titanium, distributes a load on the joint reducing localized stress points produced by opposing asperity peaks in the load-bearing surfaces of the bore and trunnion.

19 Claims, 3 Drawing Sheets

COATED LOAD BEARING SURFACE FOR A PROSTHETIC JOINT

CROSS REFERENCE TO RELATED APPLICATION

Not Applicable.

STATEMENT REGARDING FEDERALLY SPONSORED RESEARCH

Not Applicable.

FIELD OF THE INVENTION

The present invention relates generally to prosthetic joints, and more particularly to a prosthetic joint having a load bearing surface with layer of material disposed thereon.

BACKGROUND OF THE INVENTION

Prosthetic or artificial joints replace a natural joint that has degenerated from disease or has been damaged by trauma. Prosthetic joints allow a recipient to maintain a quality of life not possible without replacement of the nonfunctional natural joint.

FIG. 1 shows one known type of prosthetic joint in the form of a hip joint 10 having a femoral component 12 and a ceramic hip head or ball 14. The hip head 14 has a bore 16 defining a frustro-conical or tapered inner surface 18 and the femoral component 12 includes a metal trunnion 20 defining a tapered surface 22. The trunnion 20 is adapted for friction fit engagement into the bore 16 of the hip head.

The femoral component 12 includes a first end defining a stem portion 24 implantable within the medullary canal of a femur and a second end defining a neck portion 24 and the trunnion 20. The hip head 14 cooperates with a prosthetic acetabular cup in an acetabular socket (not shown). The hip head 14 is rotatable within the acetabular cup to allow movement of the femur with respect to the pelvic structure of a patient.

The hip joint must bear the entire body weight of a recipient thereby requiring materials able to withstand significant loading. A hip head formed from a ceramic material is desirable due to the exceptional hardness of the material and the smooth surface finish which provides long wear and smooth gliding at an interface between the hip head and an acetabular cup into which the head is inserted. However, a ceramic hip head can be relatively brittle and subject to fracture.

The hip head bore 16 and trunnion 20 have precision machined load-bearing mating surfaces. Even if efforts are made to achieve the smoothest surface possible, surface imperfections remain. FIGS. 2A–2B show the surfaces 18,22 of the bore and trunnion in more detail. The bore and trunnion surfaces 18,22 each include respective asperities in the form of peaks 26,27 and valleys 28,29 and various surface undulations. It should be understood that throughout the drawings the asperities are shown in exaggeration for the purpose of illustration and that the prosthetic joint components are not drawn to scale.

Upon insertion of the trunnion 20 into the bore 16, a peak 26 in the surface 18 of the bore disposed opposite a peak 27 in the surface 22 of the trunnion can locally concentrate stress at a point 30 thereby overstressing the ceramic ball 14 and causing it to fracture. It will be appreciated that many such localized stress points can exist after mating of the trunnion 20 and the bore 16. Loading of the joint will exacerbate the localized stressing of the bore 16 and trunnion 20 interface.

It will be appreciated by one of ordinary skill in the art that the localized concentration of stress at opposing asperity peaks increases as the taper angle of the bore and trunnion decreases. The taper angle is defined as the angle formed by the bore surface and a longitudinal axis of the bore, and similarly for the trunnion. As is known in the art, smaller taper angles are desirable to provide a more secure engagement of the bore and trunnion to reduce the risk of disassembly in use and reduce the amount of hip head material required for the bore. Disadvantageously however, smaller taper angles magnify a wedge effect of the trunnion into the bore thereby increasing the likelihood of fracturing the hip head.

It will further be appreciated by an ordinary practitioner in the art that smaller diameter hip heads are desirable to reduce friction and allow greater offsets, and are well-suited for patients having a relatively modest frame. However, smaller hip heads provide less material to support loading of the joint and are thus more susceptible to fatigue fractures, thereby limiting their utility.

FIG. 3 shows one prior art solution to reduce the tendency of a ceramic hip head 50 to fracture. The configuration includes a metallic sleeve 52 having a tapered outer surface 54 corresponding to a tapered bore 56 in the hip head and a tapered inner surface 58 corresponding to a tapered surface 60 of a trunnion 62. For example, the ceramic hip head bore 56 has a taper angle of six degrees with respect to a longitudinal axis of the bore and the trunnion 62 has a taper angle of about three degrees. As one skilled in the art can appreciate, the sleeve must be manufactured to precise dimensions, tolerances, and surface finishes to complement the contour of a hip head bore on one surface and the trunnion on an opposing surface of the sleeve. Not only is such a sleeve complex and costly to manufacture, it does not eliminate local stress concentration at points where opposing asperity peaks are in proximity to one another. Furthermore, the trunnion is subject to disassembly in use as compared with a bore and trunnion each having a taper angle of three degrees, for example.

SUMMARY OF THE INVENTION

The present invention overcomes the aforesaid and other disadvantages by providing a prosthetic hip joint including a ceramic hip head having a tapered bore defining an inner surface wherein the inner surface has asperities in the form of peaks and valleys. At least a portion of the inner surface of the bore is coated with a layer of malleable material to cover the asperities thereby removing stress concentration points.

A prosthetic hip joint in accordance with the present invention can further include a femoral component having a trunnion with a tapered surface complementary to the taper of the bore. The trunnion surface can also include surface imperfections in the form of peaks and valleys. The trunnion is frictionally engageable within the bore, wherein the tapered surfaces of the trunnion and bore are adapted for bearing a load on the joint. The layer of malleable material disposed on the inner surface of the bore flows under loading of the joint and tends to fill in the valleys and cover peaks associated with the surfaces of the bore and trunnion. The layer of material distributes a load on the joint about the inner surface of the bore and the load bearing surface of the trunnion thereby reducing local stress concentration points where respective peaks in surfaces of the bore and trunnion are in close proximity. Furthermore, the layer of material enhances the frictional engagement of the trunnion and bore, thus reducing the risk of disassembly in use.

In another embodiment, a prosthetic hip joint includes a trunnion defining an outer surface and a layer of malleable material disposed on at least a portion of the outer surface of the trunnion. The trunnion is adapted for insertion into a corresponding bore in a hip head, wherein the layer of material distributes a load on the joint about the interface surfaces of the respective bore and trunnion.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
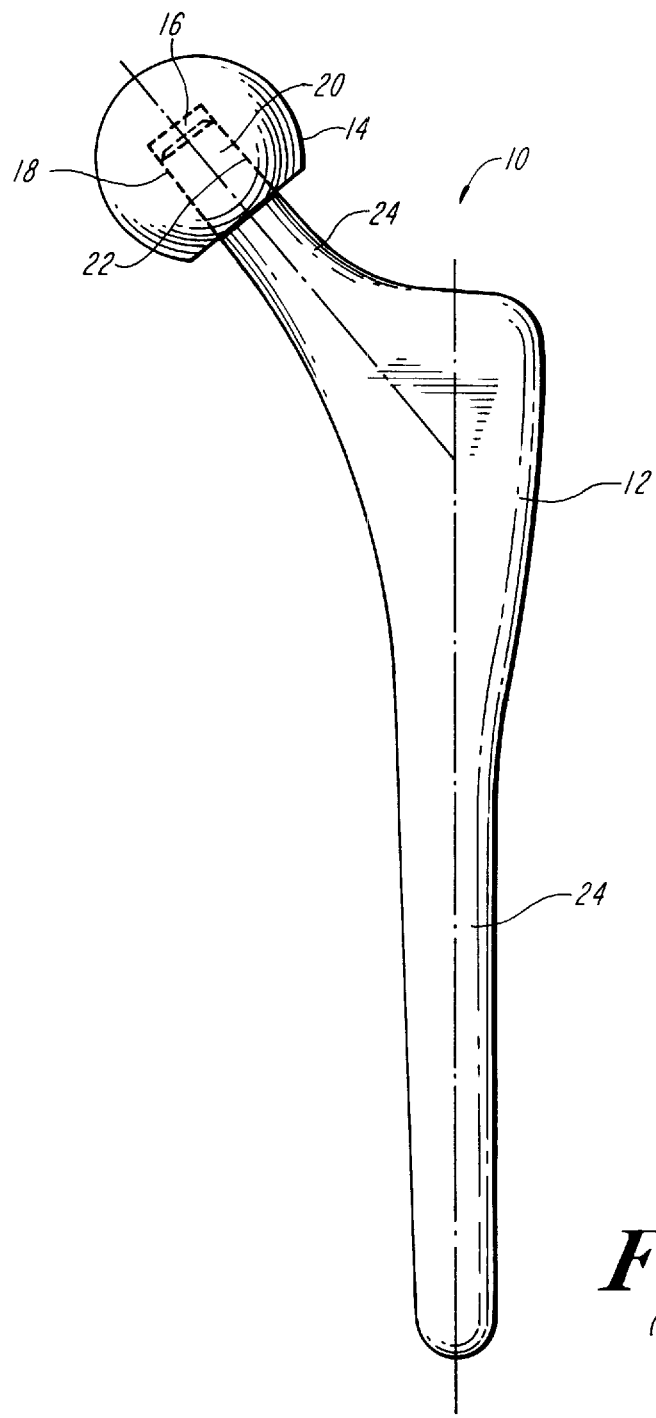
FIG. 1 is a prior art schematic representation of a prosthetic hip joint.
Figure 2A:
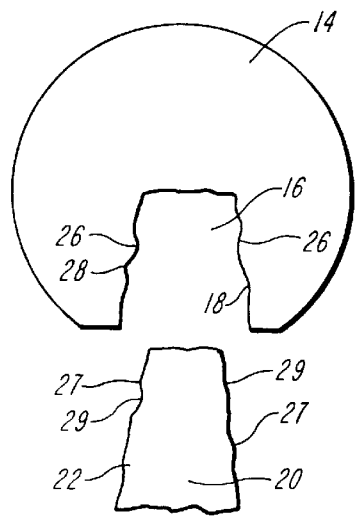
FIG. 2A is a prior art schematic diagram of surfaces of a ceramic hip head and corresponding trunnion prior to engagement, which forms a portion of the prosthetic hip joint of FIG. 1.
Figure 2B:
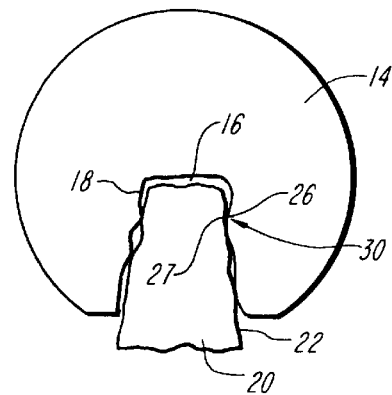
FIG. 2B is a prior art schematic diagram of the hip head and trunnion of FIG. 2A, shown in an engaged position.
Figure 3:
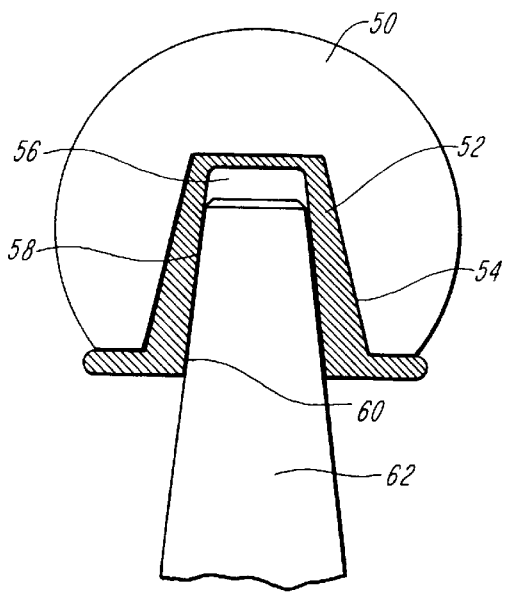
FIG. 3 is a prior art schematic diagram of a prosthetic joint having a sleeve interposed between a bore and trunnion.
Figure 4A:
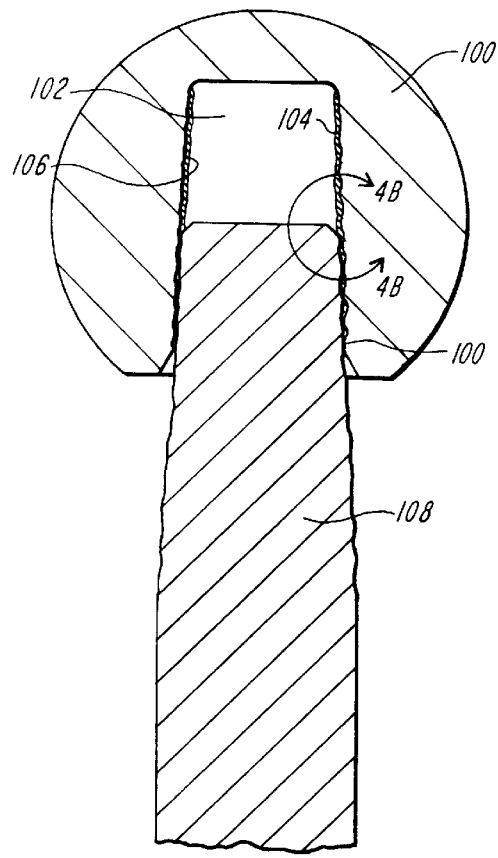
FIG. 4A is a prosthetic hip joint in accordance with the present invention.
Figure 4B:
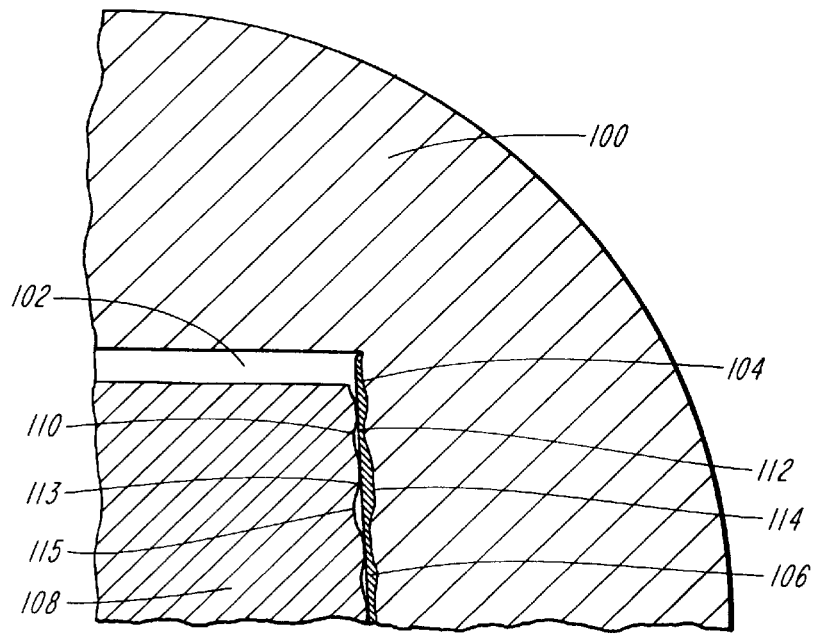
FIG. 4B is an enlarged cross sectional view of a portion of the prosthetic hip joint of FIG. 4A.

Referring to FIGS. 4A–4B, a prosthetic hip joint in accordance with the present invention includes a ceramic hip head 100 having a tapered bore 102 defining an inner surface 104 with a layer of malleable material 106 deposited on a portion of the inner surface to provide a coated surface. A trunnion 108 defines an outer surface 110 adapted for insertion into the bore 102, so as to frictionally engage the trunnion and bore. The inner surface 104 of the bore forms a taper angle with respect to a longitudinal axis of the bore and the trunnion 108 has a taper angle complementing the taper angle of the bore. The inner surface 104 of the bore and the outer surface 110 of the trunnion bear a load on the joint.

The surfaces 104,110 of the bore and trunnion have asperities, or surface imperfections, in the form of respective peaks 112,113 and valleys 114,115. The layer of malleable material 106 covers or coats the peaks 112 in the surface of the bore 102. Under pressure, such as from a load on the joint, the material 106 flows into the valleys 114 in such a way so as to distribute the load about the surfaces 104,110 of the ceramic hip head 100 and the trunnion 108. The malleable material 106 eliminates localized stress concentration caused by opposing peaks 112,113 in the surfaces of the bore and trunnion. Also, by providing a more intimate fit, the friction fit between the trunnion and bore is enhanced, thus reducing the likelihood of disassembly in use.

The hip head 100 is formed from a ceramic material to provide an inert, hard, abrasion resistant, and bio-compatible component. In one embodiment, the hip head is formed from alumina ($Al_2O_3$). In another embodiment, the hip head is formed from zirconium dioxide ($ZrO_2$). A yttrium or magnesium stabilizer can be added to the ceramic material as is known to one of ordinary skill in the art. Ceramics provide certain advantages over metals and metal alloys. In addition, ceramics can provide a superior surface finish and produce less friction than a metal during articulation of the joint.

In one embodiment, the layer of material 106 is pure titanium deposited on the bore surface. Other materials having suitable properties can be used to coat the bore surface such as titanium alloys, gold, silver, platinum and tantalum. Still, other materials can be used provided the material can adhere to a ceramic, is malleable, is biocompatible, and has galvanic compatibility with common trunnion materials, such as cobalt-chromium and titanium alloys.

In an exemplary embodiment, the malleable layer (e.g., titanium) is deposited on the bore surface using low temperature plasma deposition to avoid thermal shock to the ceramic hip head which can cause fracturing. Other suitable processes known to one skilled in the art can also be used to deposit the layer of material, such as ion beam sputter deposition, physical vapor deposition, and chemical vapor deposition. The thickness of the pure titanium layer should be about at least twelve millionths (0.000012) of an inch. More preferably, however, the thickness of the layer of malleable material can range from about 0.00001 inch to 0.010 inch. A most preferred thickness is about 0.0001 inch.

Although the layer of material 106 is shown as a continuous coating on the surface 104 of the bore, in other embodiments the material covers only a portion of the surface of the bore or trunnion. The material can be strategically placed at particular locations where the surfaces will meet, or at known stress points. In further embodiments, the material is deposited on a surface in predetermined patterns, such as stripes and discrete shapes (e.g., circles).

In an illustrative embodiment, the ceramic hip head 100 has a diameter of about twenty-eight millimeters and the surface 104 of the bore 102 has a taper angle of about three degrees. A smaller degree taper angle provides a more secure fit whereby the trunnion is less easily removed from the bore so as to reduce the risk of disassembly in use. For example, a trunnion engaged in a corresponding bore with taper angle of three degrees provides a more secure engagement than a six degree taper angle, all else being equal. In an illustrative embodiment, the bore 102 has a depth of about 0.6 inch and a diameter of about 0.5 at an entry of the bore. Other hip head diameters and taper angles are possible. For example, in other embodiments, the hip head has a diameter of about twenty-two millimeters, but could be larger and smaller. Also, other taper angles can be used, such as six and nine degrees or other angles.

Figure 5:
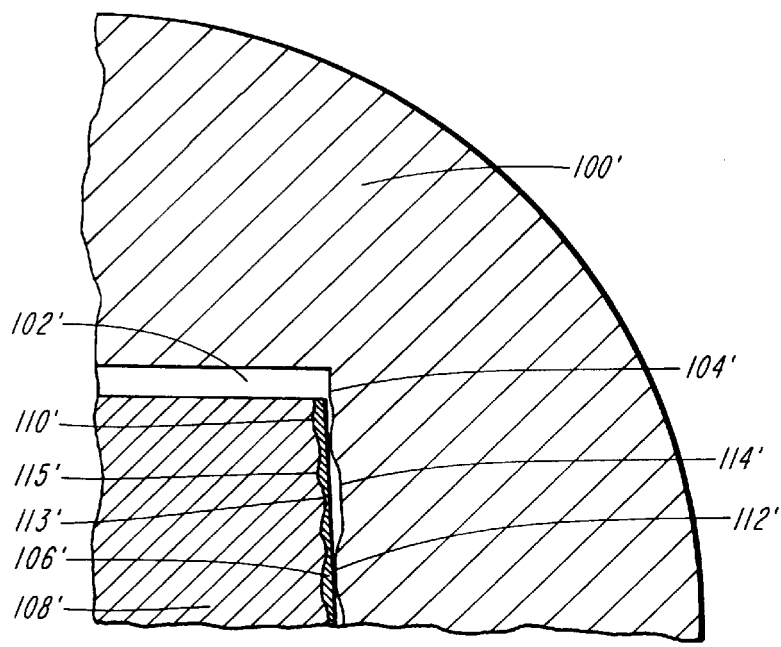
FIG. 5 is an enlarged cross sectional view of a portion of a further embodiment of the prosthetic hip joint of FIG. 4A.

In another embodiment shown in FIG. 5, a prosthetic hip joint includes a ceramic hip head 100' defining a bore 102' which is mateable with a trunnion 108' of a femoral component. The trunnion 108' has a layer of material 106' on at least a portion thereof for distributing a load on the joint. The material 106', such as titanium, covers peaks 112',113' and fills valleys 114',115' in load-bearing surfaces 104',110 so as to prevent localized stress areas caused by mutually interfering asperities 112', 113'. By providing the layer of material 106' on the trunnion, corrosion of the trunnion is reduced or eliminated due to galvanic compatibility of the trunnion alloy and the layer of material.

The above-described embodiments of a prosthetic hip joint allow the use of smaller diameter hip heads as compared with joints not having a malleable layer of material on bore and/or trunnion surfaces. Also, small bore taper angles can be used with small hip heads of varying offsets while not sacrificing structural integrity of the hip head. Further, a smaller diameter hip head advantageously produces less friction and less wear debris. Smaller taper angles provide certain design advantages. Moreover, a greater range of offset is possible using a three degree taper that is coated according to the present invention, than with a prior art three degree taper.

One skilled in the art will realize further features and advantages of the invention from the above-described embodiments. Accordingly, the invention is not to be limited by what has been particularly shown and described, except as indicated by the appended claims.

What is claimed is:

1. A prosthetic hip joint, comprising:
    a ceramic hip head including a bore defined by an inner surface, the bore having a taper angle with respect to a longitudinal axis of the bore, the inner surface having asperities; and
    a coating of malleable material deposited on at least a portion of the inner surface of the bore, the malleable material substantially coating the asperities in the inner surface so as to provide a smooth surface and to substantially reduce localized stress concentration points.

2. The prosthetic hip joint according to claim 1, further comprising a femoral component including a trunnion having a tapered surface for friction fit insertion into the bore of the ceramic hip head.

3. The prosthetic hip joint according to claim 2, wherein the tapered surface of the trunnion includes surface asperities.

4. The prosthetic hip joint according to claim 1, wherein the coating of material comprises titanium.

5. The prosthetic hip joint according to claim 4, wherein the titanium coating is greater than about twelve millionths of an inch.

6. The prosthetic hip joint according to claim 1, wherein the coating of material is pure titanium.

7. The prosthetic hip joint according to claim 1, wherein the coating of material is selected from the group consisting of pure titanium, a titanium alloy, gold, silver, platinum, and tantalum.

8. The prosthetic hip joint according to claim 1, wherein the ceramic hip head is formed from a material including alumina.

9. The prosthetic hip joint according to claim 1, wherein the ceramic hip head is formed from a material including zirconium dioxide.

10. The prosthetic hip joint according to claim 1, wherein the ceramic hip head is formed from a material including a yttrium stabilizer.

11. The prosthetic hip head according to claim 1, wherein the ceramic hip head is formed from a material including a magnesium stabilizer.

12. The prosthetic hip head according to claim 2, wherein the trunnion is formed from metal.

13. The prosthetic hip joint according to claim 1, wherein the taper angle of the bore is less than or equal to about three degrees.

14. The prosthetic hip joint according to claim 1, wherein the taper angle of the bore is less than or equal to about six degrees.

15. The prosthetic hip joint according to claim 1, wherein a diameter of the hip head is less than or equal to about 28 millimeters.

16. The prosthetic hip joint according to claim 3, wherein a diameter of the hip head is less than or equal to about 22 millimeters.

17. A prosthetic hip joint, comprising:
    a ceramic hip head having a bore defining a cylindrical surface having a taper angle with respect to a longitudinal axis of the bore, the cylindrical surface having imperfections defined by peaks and valleys;
    a femoral component including a trunnion defining an outer surface having a taper angle with respect to a longitudinal axis of the trunnion, the taper angle of the trunnion being complementary to the taper angle of the bore, the trunnion being insertable into the bore for frictional engagement of the bore and trunnion; and
    a coating of pure titanium applied to at least a portion of the cylindrical surface of the bore, the titanium substantially coating the imperfections in the cylindrical surface of the bore so as to provide a smooth surface and to prevent localized stress concentration points when inserting the trunnion into the bore.

18. A prosthetic hip joint, comprising:
    a femoral component including a trunnion defining a surface, the surface having a taper with respect to a longitudinal axis of the trunnion, the surface having surface imperfections; and
    a coating of malleable material deposited on at least a portion of the surface of the trunnion, the malleable material substantially coating the surface imperfections in the coated portion of the trunnion surface so as to provide a generally smooth surface and to substantially reduce localized stress concentration points.

19. The prosthetic hip joint according to claim 18, wherein the coating of material is pure titanium.

* * * * *